(12) United States Patent
Ichiki et al.

(10) Patent No.: US 11,025,812 B2
(45) Date of Patent: Jun. 1, 2021

(54) IMAGING APPARATUS, IMAGING METHOD, AND IMAGING SYSTEM

(71) Applicant: SONY CORPORATION, Tokyo (JP)

(72) Inventors: Hiroshi Ichiki, Kanagawa (JP); Isamu Nakao, Tokyo (JP); Tetsuro Kuwayama, Tokyo (JP); Noriyuki Kishii, Kanagawa (JP); Yusaku Nakashima, Tokyo (JP); Takeshi Matsui, Tokyo (JP)

(73) Assignee: SONY CORPORATION, Tokyo (JP)

( * ) Notice: Subject to any disclaimer, the term of this patent is extended or adjusted under 35 U.S.C. 154(b) by 250 days.

(21) Appl. No.: 16/067,662

(22) PCT Filed: Nov. 16, 2016

(86) PCT No.: PCT/JP2016/083905
§ 371 (c)(1),
(2) Date: Jul. 2, 2018

(87) PCT Pub. No.: WO2017/138210
PCT Pub. Date: Aug. 17, 2017

(65) Prior Publication Data
US 2020/0267305 A1 Aug. 20, 2020

(30) Foreign Application Priority Data
Feb. 12, 2016 (JP) .............. JP2016-024859

(51) Int. Cl.
*H04N 5/232* (2006.01)
*G06T 7/80* (2017.01)
(Continued)

(52) U.S. Cl.
CPC ....... *H04N 5/23212* (2013.01); *A61B 5/0261* (2013.01); *G06T 7/80* (2017.01); *H04N 5/2256* (2013.01)

(58) Field of Classification Search
None
See application file for complete search history.

(56) References Cited

U.S. PATENT DOCUMENTS

| 2004/0015327 A1* | 1/2004 | Sachdeva | A61C 7/002 |
| | | | 702/167 |
| 2010/0128972 A1* | 5/2010 | Koizumi | G06T 7/593 |
| | | | 382/154 |

(Continued)

FOREIGN PATENT DOCUMENTS

| JP | 5-071918 A | 3/1993 |
| JP | 05-071918 A | 3/1993 |
| JP | 2014-225843 A | 12/2014 |

OTHER PUBLICATIONS

International Search Report and Written Opinion of PCT Application No. PCT/JP2016/083905, dated Feb. 7, 2017, 08 pages of ISRWO.

*Primary Examiner* — Clifford Hilaire
(74) *Attorney, Agent, or Firm* — Chip Law Group

(57) ABSTRACT

To provide an image analyzing technology capable of obtaining an image with less shading and with enough speckle contrast. An imaging apparatus includes: a light source that irradiates an imaging object with coherent light with a first irradiation condition and a second irradiation condition; a speckle imaging unit that captures a first speckle image obtained from scattered light of the imaging object irradiate at the first irradiation condition, and a second speckle image obtained from scattered light of the imaging object irradiate at the second irradiation condition; and an information processing unit that separates speckle images at boundaries of average luminance difference formed in the first speckle image and the second speckle image, connecting the separaged speckle images at the boundaries, and analyzes the combined speckle combined image.

11 Claims, 7 Drawing Sheets

(51) Int. Cl.
*A61B 5/026* (2006.01)
*H04N 5/225* (2006.01)

(56) References Cited

U.S. PATENT DOCUMENTS

| | | | |
|---|---|---|---|
| 2013/0218531 A1* | 8/2013 | Deichmann | A61C 13/0004 |
| | | | 703/1 |
| 2014/0153820 A1* | 6/2014 | Lee | G06T 5/007 |
| | | | 382/162 |
| 2014/0340543 A1 | 11/2014 | Nakada et al. | |

* cited by examiner

IMAGING APPARATUS, IMAGING METHOD, AND IMAGING SYSTEM

CROSS REFERENCE TO RELATED APPLICATIONS

This application is a U.S. National Phase of International Patent Application No. PCT/JP2016/083905 filed on Nov. 16, 2016, which claims priority benefit of Japanese Patent Application No. JP 2016-024859 filed in the Japan Patent Office on Feb. 12, 2016. Each of the above-referenced applications is hereby incorporated herein by reference in its entirety.

TECHNICAL FIELD

The present technology relates to an imaging apparatus and, more particularly, to an imaging apparatus, an imaging method, and an imaging system capable of detecting a focus for capturing a speckle image.

BACKGROUND ART

In the related art, in order to grasp the shape, structure, and the like of a biological sample such as a blood vessel or a cell, an imaging apparatus and an imaging method using an optical method have been developed (refer to Patent Literature 1).

In an imaging system disclosed in Patent Literature 1, an interference light image by light obtained by reflection of light from a light emitting unit on an object and interference is captured at a first timing, and a luminescent image of the light emitted from the object is captured at a second timing.

On the other hand, in an imaging technique using an optical method in the case of using a flow path such as a blood vessel as an imaging object, there is a concern that occurrence of various noises may cause detection accuracy to deteriorate. As one of the noises, speckle is known. The speckle is a phenomenon in which a spot-like swaying pattern appears on an irradiated surface depending on an uneven shape of the irradiated surface. In recent years, techniques have also been developed with respect to a method of imaging a flow path such as a blood vessel by using speckle which is one of the noises.

Speckle is a random interference/diffraction pattern due to scattering or the like in an optical path. In addition, the magnitude of speckle is represented by an index called speckle contrast which is a value obtained by dividing the standard deviation of the intensity distribution by the average of the intensity distribution. When the imaging object irradiated with coherent light is observed by using an imaging optical system, the speckle caused by scattering of the imaging object is observed on the image plane. Then, when the imaging object moves or changes in shape, a random speckle pattern corresponding to the movement or change is observed.

When a light scattering fluid such as blood is observed, the speckle pattern changes at every moment according to the change in fine shape caused by the flow. At that time, when an imaging element is arranged on the image plane and the fluid is imaged with an exposure time sufficiently longer than change of the speckle pattern, the speckle contrast of a portion in which the blood is flowing, that is, a portion of the blood vessel is reduced in time average. Angiography can be performed by using such a change in speckle contrast.

CITATION LIST

Patent Literature

Patent Literature 1: JP-A-2009-136396

DISCLOSURE OF INVENTION

Technical Problem

In the imaging apparatus using such speckles, since the speckle pattern is measured by a monocular camera, the focus of the imaging cannot be identified as compared with the normal bright field imaging. In addition, there are problems of large particle noise caused by speckle, incapability of acquiring depth information of an image to be captured, and the like.

In view of this, a main object of the present technology is to provide an imaging technique capable of reducing a noise in a captured speckle image.

Solution to Problem

According to the present technology, there is provided an imaging apparatus, including: a coherent light source that irradiates an imaging object with coherent light; a first speckle imaging unit that captures a speckle image obtained from scattered light of the imaging object irradiated with the coherent light; a second speckle imaging unit that captures a speckle image obtained from scattered light of the imaging object irradiated with the coherent light; and an image combination unit that combines the first speckle image captured by the first speckle imaging unit and the second speckle image captured by the second speckle imaging unit.

The imaging apparatus may further include an image superimposing unit that superimposes image information of the first speckle image and image information of the second speckle image on each other.

Further, the imaging apparatus may further include: a parallax information obtaining unit that obtains parallax information generated between the first speckle imaging unit and the second speckle imaging unit; and an image processing unit that obtains state information of the imaging object on the basis of the parallax information obtained by the parallax information obtaining unit.

Further, according to the imaging apparatus of the present technology, each of the first speckle imaging unit and second speckle imaging unit may include a pixel unit, the pixel unit including pixels each corresponding to each color component of a plurality of color components arrayed on a plane regularly. In the imaging apparatus, the pixel unit may be a pixel unit of Bayer matrix.

According to the present technology, there is provided an imaging system, including: a coherent light source that irradiates an imaging object with coherent light; a first speckle imaging device that captures a speckle image obtained from scattered light of the imaging object irradiated with the coherent light; a second speckle imaging device that captures a speckle image obtained from scattered light of the imaging object irradiated with the coherent light; and an image combination device that combines the first speckle image captured by the first speckle imaging device and the second speckle image captured by the second speckle imaging device.

The imaging system may further include an image superimposing device that superimposes image information of the first speckle image and image information of the second speckle image on each other.

Further, the imaging system may further include: a parallax information obtaining device that obtains parallax information generated between the first speckle imaging device and the second speckle imaging device; and an image processing device that obtains state information of the imaging object on the basis of the parallax information obtained by the parallax information obtaining device.

Further, according to the imaging system, each of the first speckle imaging device and second speckle imaging device may include a pixel unit, the pixel unit including pixels each corresponding to each color component of a plurality of color components arrayed on a plane regularly. In the imaging system, the pixel unit may be a pixel unit of Bayer matrix.

According to the present technology, there is provided an imaging method, including: a coherent light irradiating step of irradiating an imaging object with coherent light; a first first speckle imaging step of capturing a speckle image obtained from scattered light of the imaging object irradiated with the coherent light; a second first speckle imaging step of capturing a speckle image obtained from scattered light of the imaging object irradiated with the coherent light; and an image combining step of combining the first speckle image captured in the first first speckle imaging step and the second speckle image captured in the second first speckle imaging step.

Advantageous Effects of Invention

According to the present technology, since the image combination unit is provided, it is possible to reduce a noise in a captured image, and thereby to capture a speckle image with a high resolution.

In addition, the effects described herein are not necessarily limited and may be any of the effects that are intended to be described in the present technology.

MODE(S) FOR CARRYING OUT THE INVENTION

Suitable embodiments for implementing the present technology will be described below with reference to the drawings. Each embodiment described below illustrates an example of a representative embodiment of the present technology, so that the scope of the present technology is not to be narrowly interpreted by the embodiments. In addition, the description will be made in the following order.

Figure 1:
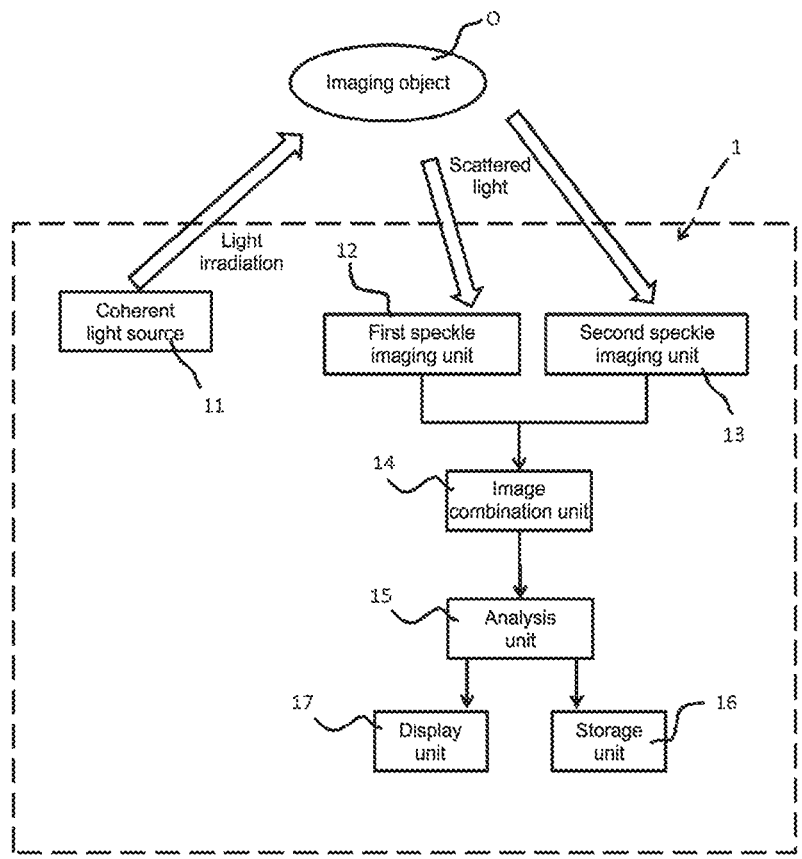
FIG. 1 is a schematic conceptual diagram schematically illustrating a concept of a first embodiment of an imaging apparatus according to the present technology.

1. Imaging Apparatus according to First Embodiment
(1) Coherent Light Source
(2) First Speckle Imaging Unit
(3) Second Speckle Imaging Unit
(4) Image Combination Unit
(5) Analysis Unit
(6) Storage Unit
(7) Display Unit
(8) Imaging Object
2. Imaging Apparatus according to Second Embodiment
(1) Image Superimposing Unit
3. Imaging Apparatus according to Third Embodiment
(1) Parallax Information Obtaining Unit
(2) Image Processing Unit
4. Imaging Apparatus according to Fourth Embodiment
(1) Pixel Unit
5. Imaging System according to Present Technology
(1) Coherent Light Source
(2) First Speckle Imaging Device
(3) Second Speckle Imaging Device
(4) Image Combination Device
(5) Analysis Device
(6) Storage Device
(7) Display Device
(8) Image Superimposing Unit
(9) Parallax Information Obtaining Device
(10) Image processing Device
6. Imaging Method according to First Embodiment
(1) Coherent Light Irradiating Step
(2) First First speckle imaging Step
(3) Second First speckle imaging Step
(4) Image combining Step
(5) Analyzing Step
(5-1) Parallax information obtaining Step
(5-2) Image processing Step
(6) Storing Step
(7) Displaying Step 1. Imaging Apparatus According to First Embodiment FIG. 1 is a schematic conceptual diagram schematically illustrating a first embodiment of an imaging apparatus according to the present technology. The imaging apparatus 1 according to the first embodiment at least includes a coherent light source 11, a first speckle imaging unit 12, a second speckle imaging unit 13, and an image combination unit 14. In addition, as necessary, the imaging apparatus may further include an analysis unit 15, a storage unit 16, a display unit 17, and the like. Each component will be described in detail below.

(1) Coherent Light Source

The coherent light source 11 irradiates the imaging object O with coherent light. The coherent light emitted from the coherent light source 11 denotes light in which the phase relationship between light waves at arbitrary two points in a light flux is invariable and constant in terms of time and, thus, even in the case of dividing the light flux by an arbitrary method and, after that, providing a large optical path difference and overlaying the divided light fluxes again, perfect coherency is exhibited.

The type of the coherent light source 11 is not particularly limited as long as the effect of the present technology is not impaired. As an example, laser light and the like may be exemplified. As the coherent light source 11 that emits laser light, an argon ion (Ar) laser, a helium-neon (He—Ne) laser, a dye laser, a krypton (Cr) laser, a semiconductor laser, a solid-state laser in which a semiconductor laser and a wavelength conversion optical element are combined, and the like may be exemplified, and one or two or more types thereof may be used freely in combination.

(2) First Speckle Imaging Unit

The imaging apparatus 1 according to the present technology includes a first speckle imaging unit 12. In this first speckle imaging unit 12, speckle imaging is performed on the basis of scattered light obtained from the imaging object O irradiated with the coherent light. Note that, in the following description, a speckle image captured by the first speckle imaging unit 12 will be referred to as "first speckle image".

The imaging method performed by the first speckle imaging unit 12 is not particularly limited as long as the effect of the present technology is not impaired, and one or two or more known imaging methods may be selected and used freely in combination. For example, an imaging method using an imaging element such as a charge coupled device (CCD) or a complementary metal oxide semiconductor (CMOS) sensor may be exemplified.

In addition, the first speckle imaging unit 12 automatically measures the luminance distribution of the speckle in the captured image. Herein, when an object illuminated by using coherent light is observed by the imaging optical system, speckle caused by scattering of the object on the image plane is observed. In the first speckle imaging unit 12, the luminance distribution of the speckle in the captured image is measured using, for example, a luminance meter. In addition, it is possible to calculate the speckle luminance distribution from an image captured from an imaging element such as a CCD or a CMOS.

The method of measuring the luminance distribution is not particularly limited as long as the effect of the present technology is not impaired, and one or two or more known calculation methods may be selected and used freely in combination.

In the first speckle imaging unit 12, for example, an image or the like in which a pseudo blood vessel through which pseudo blood flows is mapped on the basis of the speckle luminance distribution is generated. Herein, since the speckle is a random interference/diffraction pattern as described above, when the scattering fluid such as blood moves or changes with time, the speckle also varies with time. For this reason, it is possible to observe the boundary between the fluid and other portions.

Note that, in order to clarify the portion where speckle occurs, the first speckle imaging unit 12 may have a configuration where, for example, equalization is performed by using a plurality of speckle images to reduce irregularity of the speckle image.

(3) Second Speckle Imaging Unit

The imaging apparatus 1 according to the present technology includes a second speckle imaging unit 13. In this second speckle imaging unit 13, similar to the first speckle imaging unit 12, speckle imaging is performed on the basis of scattered light obtained from the imaging object O irradiated with the coherent light. In other words, the imaging apparatus 1 according to the present technology has a structure of a so-called pantoscopic imaging apparatus. In addition, each imaging unit is configured to capture a speckle image.

Further, the imaging apparatus 1 according to the present technology has a so-called stereo camera structure, in which the second speckle imaging unit 13 and the first speckle imaging unit 12 capture the imaging object O in different directions.

The structure of the second speckle imaging unit 13 is the same as the structure of the first speckle imaging unit 12, and description thereof will thus be omitted. Note that, in the following description, a speckle image captured by the second speckle imaging unit 13 will be referred to as "second speckle image".

(4) Image Combination Unit

The imaging apparatus 1 according to the present technology includes an image combination unit 14. The image combination unit 14 combines the first speckle image and the second speckle image. Specifically, for example, the image combination unit 14 combines image information (for example, number of pixels, color tone of pixels, etc.) of the first speckle image and image information of the second speckle image to thereby generate a single speckle combined image.

Herein, it is necessary to generate a speckle combined image, with which it is possible to analyze the state of the imaging object O. When the image combination unit 14 combines the first speckle image and the second speckle image, for example, the image combination unit 14 may correct the luminance value of the speckle combined image on the basis of the luminance values of the speckle images such that the luminance distribution of the speckle combined image is uniform. The correcting method is not particularly limited, and a known method may be used.

(5) Analysis Unit

The imaging apparatus 1 according to the present technology may include an analysis unit 15 as necessary. The analysis unit 15 analyzes the state of the imaging object O by using the speckle combined image generated by the image combination unit 14.

In such a case, for example, in a case where the imaging object O is a blood vessel, when the scattering fluid such as blood moves or changes with time, the speckle also varies with time accordingly. Therefore, the speed of the blood flow can be measured by the analysis unit 15.

Note that the analysis unit 15 is not necessarily included in the imaging apparatus 1 according to the present technology, and the state of the imaging object O may also be analyzed by using an external analysis device or the like.

(6) Storage Unit

The imaging apparatus 1 according to the present technology may further include a storage unit 16 that stores the speckle image captured by the first speckle imaging unit 12, the non-speckle image captured by the second speckle imaging unit 13, the speckle combined image generated by the image combination unit 14, the analysis result analyzed by the analysis unit 15, and the like.

This storage unit 16 is not necessarily included in the imaging apparatus 1 according to the present technology, but the imaging apparatus may be connected to, for example, an external storage device to store the speckle image and the like.

(7) Display Unit

The imaging apparatus 1 according to the present technology may further include a display unit 17 that displays the speckle image captured by the first speckle imaging unit 12, the non-speckle image captured by the second speckle imaging unit 13, the combined image generated by the image combination unit 14, the analysis result analyzed by the analysis unit 15, and the like. In addition, the display unit 17 may display the luminance distribution measured by the first speckle imaging unit 12 so as to be superimposed on the speckle image. The display unit 17 is not necessarily included in the imaging apparatus 1 according to the present technology, and light irradiation may be performed on the imaging object O by using, for example, an external monitor or the like.

(8) Imaging Object

Although the imaging apparatus 1 according to the present technology may set various objects as the imaging objects O, the imaging apparatus 1 can be suitably used for imaging an object containing, for example, a fluid as the imaging object O. Due to the nature of the speckle, the speckle is not easily generated from the fluid. For this reason, when the object containing a fluid is imaged by using the imaging apparatus 1 according to the present technology, a boundary between the fluid and other portions, a flow speed of the fluid and the like can be obtained.

More specifically, a biological object may be exemplified as the imaging object O, and blood may be exemplified as a fluid. For example, when the imaging apparatus 1 according to the present technology is mounted on a surgical microscope, a surgical endoscope, or the like, surgery can be performed while identifying the position of a blood vessel. Therefore, it is possible to carry out safer and highly accurate surgery, and thus, it is possible to contribute to further development of medical technology.

In the imaging apparatus 1 according to the first embodiment as described above, the first speckle imaging unit 12 and the second speckle imaging unit 13, i.e., two imaging units, are provided, and a so-called stereo camera structure is employed. So there is parallax between the two imaging units.

As a result, wavefront information of the imaging object O that reaches the first speckle imaging unit 12 is different from wavefront information of the imaging object O that reaches the second speckle imaging unit 13. The image noise resulting from the speckle shape of the first speckle image is different from the image noise resulting from the speckle shape of the second speckle image.

To the contrary, according to the present technology, the imaging apparatus 1 includes the image combination unit 14. The image combination unit 14 combines the first speckle image and the second speckle image, and the noise is thus averaged. So the image noise of the speckle combined image may be reduced. As a result, it is possible to acquire the speckle combined image with high resolution.

Therefore, for example, when a blood vessel in which blood is flowing is imaged, a change of speckles according to temporal fluctuation of blood can be observed, so that it is possible to acquire an image by which it is possible to accurately recognize the flow path of the blood corpuscles. As a result, it is possible to accurately observe the relative position of the blood vessel to the biological tissue (for example, the heart or the like).

Further, according to the imaging apparatus 1 of the present technology, both the imaging units 12 and 13 capture speckles. So, even if one imaging unit does not work, the other imaging unit may capture a speckle. As a result, a user may keep on observing the imaging object O. Therefore, for example, if the imaging apparatus 1 of the present technology is used for medical operations, even if one imaging unit does not work, a doctor may continue the operation.

2. Imaging Apparatus According to Second Embodiment

Figure 2:
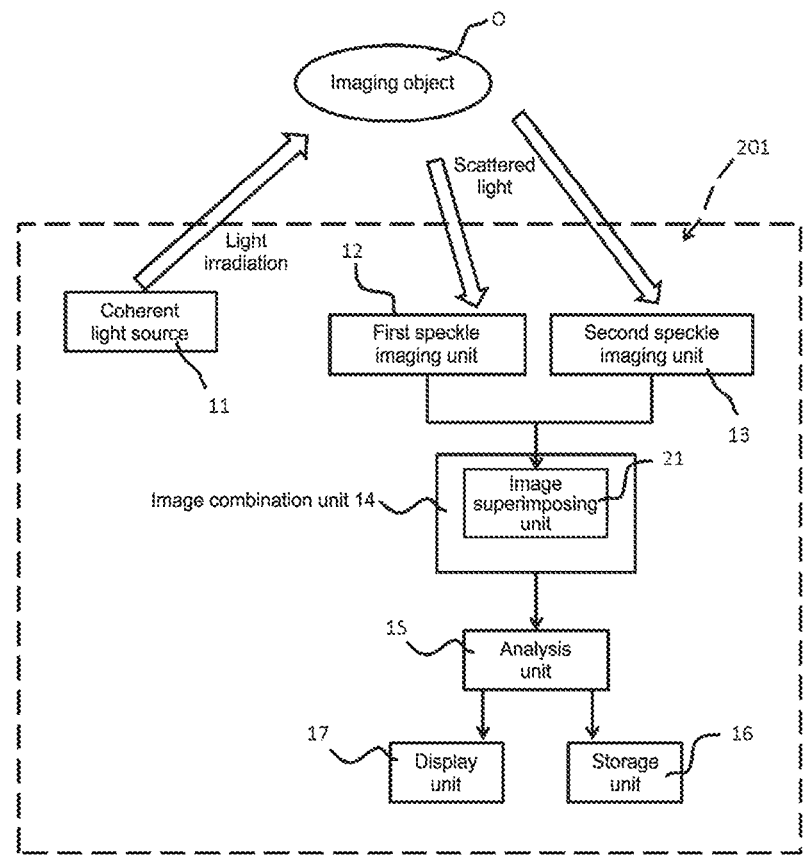
FIG. 2 is a schematic conceptual diagram schematically illustrating a concept of a second embodiment of the imaging apparatus according to the present technology.

FIG. 2 is a schematic conceptual diagram illustrating an imaging apparatus according to a second embodiment to which the present technology can be applied.

The imaging apparatus 201 according to the second embodiment is different from the imaging apparatus 1 according to the first embodiment in that the image combination unit 14 includes an image superimposing unit 21.

On the other hand, the embodiments are the same in that at least the coherent light source 11, the first the first speckle imaging unit 12, the second speckle imaging unit 13, and the image combination unit 14 are included, and furthermore, the embodiments are the same in that the analysis unit 15, the storage unit 16, the display unit 17, and the like may be included as necessary.

Therefore, in the following description of the imaging apparatus 201 according to the second embodiment, the description of the configuration common to the imaging apparatus 1 according to the first embodiment will be omitted. Hereinafter, the image superimposing unit 21 will be described.

(1) Image Superimposing Unit

The imaging apparatus 201 according to the second embodiment includes an image superimposing unit 21. When the image combination unit 14 combines the first speckle image and the second speckle image, the image superimposing unit 21 superimposes image information of the speckle images. The superimposing method is not particularly limited, and a known method may be used. For example, a method of adding and averaging speckle images may be used.

Effects of the imaging apparatus 201 including the image superimposing unit 21 of the second embodiment are the same as effects of the imaging apparatus 1 of the first embodiment. Especially, since the imaging apparatus 201 includes the image superimposing unit 21, by combining the first speckle image and the second speckle image, the noise is averaged. Therefore the image noise of the speckle combined image may be reduced. As a result, it is possible to acquire the speckle combined image with high resolution.

3. Imaging Apparatus According to Third Embodiment

Figure 3:
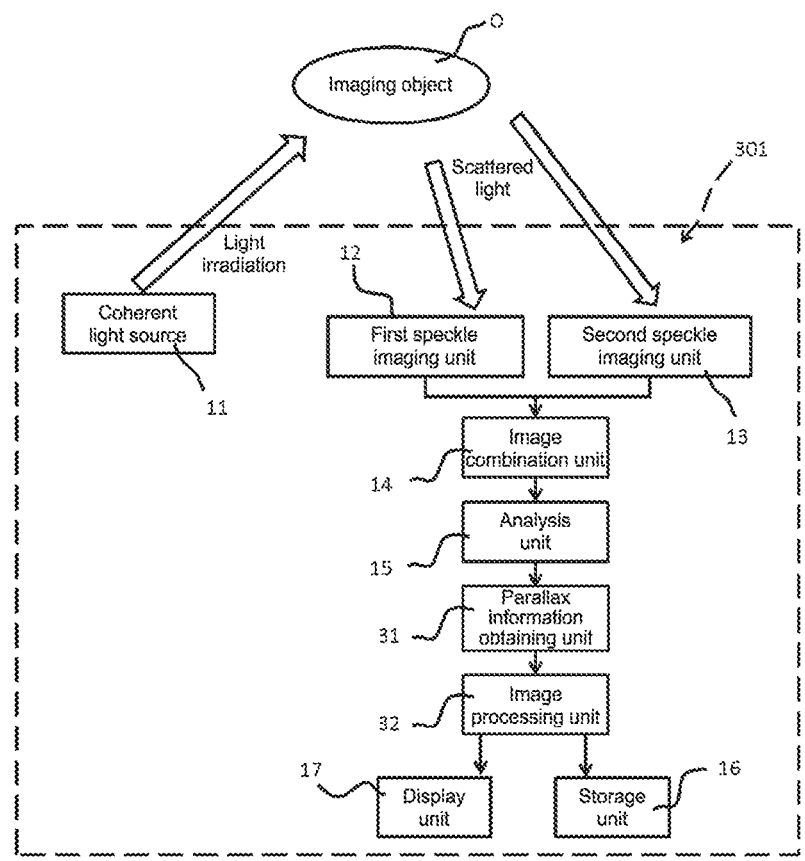
FIG. 3 is a schematic conceptual diagram schematically illustrating a concept of a third embodiment of the imaging apparatus according to the present technology.

FIG. 3 is a schematic conceptual diagram of an imaging apparatus according to a third embodiment to which the present technology is applied.

The imaging apparatus 301 according to the third embodiment is different from the imaging apparatus 1 according to the first embodiment in that the imaging apparatus 1 includes a parallax information obtaining unit 31 that obtains parallax information between the two imaging units 12 and 13, the analysis unit 15 includes an image processing unit 32, and the display unit 17 three-dimensionally displays the imaging object O in a stereo system.

On the other hand, the embodiments are the same in that at least the coherent light source 11, the first first speckle imaging unit 12, the second speckle imaging unit 13, and the image combination unit 14 are included, and furthermore, the embodiments are the same in that the analysis unit 15, the storage unit 16, the display unit 17, and the image superimposing unit 21 may be included as necessary.

For this reason, in the following description of the imaging apparatus 301 according to the third embodiment, the description of the configuration common to the imaging apparatus 1 according to the first embodiment will be omitted. Hereinafter, the parallax information obtaining unit 31 and the image processing unit 32 will be described.

(1) Parallax Information Obtaining Unit

As described above, the imaging apparatus of the present technology includes the first speckle imaging unit 12 and the second speckle imaging unit 13, i.e., two imaging units, and employs a so-called stereo camera structure. So there is parallax between the two imaging units.

The parallax information obtaining unit 31 obtains information about the parallax. The parallax information means, for example, numerical data of parallax of each speckle image. The method of obtaining information of the parallax information obtaining unit 31 is not particularly limited, and a known method may be used.

(2) Image Processing Unit

In the imaging apparatus 301 according to a third embodiment, the analysis unit 15 includes the image processing unit 32.

The image processing unit 32 is configured to obtain state information of the imaging object O on the basis of parallax information obtained by the parallax information obtaining unit 31.

As described above, in the imaging apparatus 301 according to the third embodiment, the display unit 17 three-dimensionally displays the imaging object O in a stereo system. In this case, the display unit 17 may three-dimensionally display the imaging object O only with horizontal parallax because vertical parallax is not captured.

According to the imaging apparatus 301 including the parallax information obtaining unit 31 and the image processing unit 32 of the third embodiment, the display unit 17 may three-dimensionally display a speckle combined image only with horizontal parallax. Therefore, the imaging object O may be observed not only two-dimensionally but also three-dimensionally. Therefore, for example, when imaging blood that is scattering fluid, three-dimensional information of a blood vessel in which the blood flows may be obtained.

4. Imaging Apparatus According to Fourth Embodiment

Figure 4:
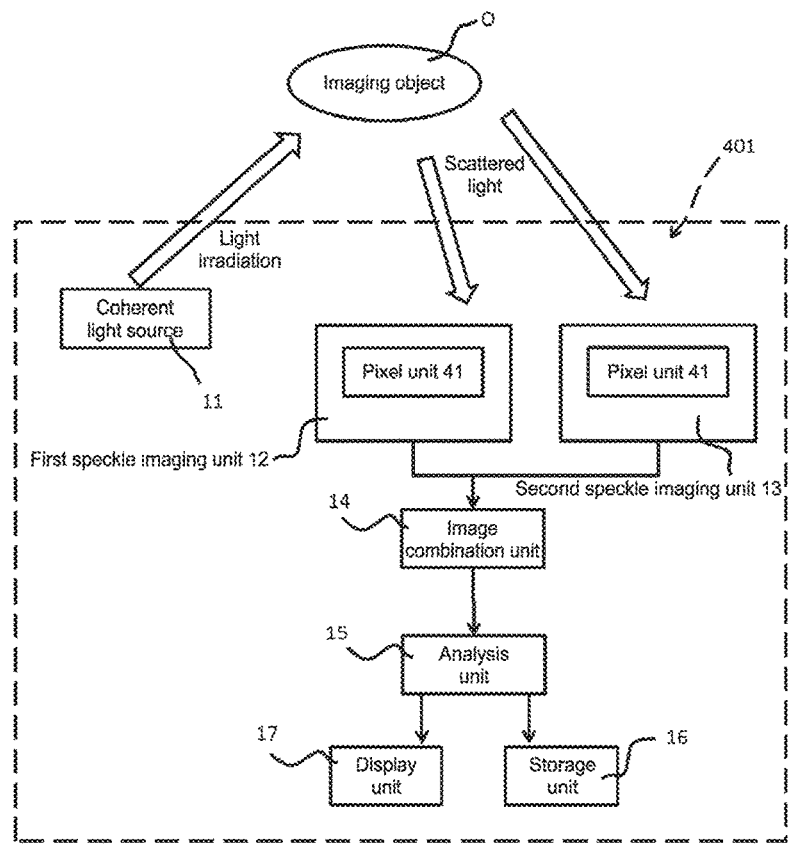
FIG. 4 is a schematic conceptual diagram schematically illustrating a concept of a fourth embodiment of the imaging apparatus according to the present technology.

FIG. 4 is a schematic conceptual diagram of an imaging apparatus according to a fourth embodiment to which the present technology is applied.

The imaging apparatus 301 according to the fourth embodiment is different from the imaging apparatus 1 according to the first embodiment in that each of the first speckle imaging unit 12 and the second speckle imaging unit 13 includes a pixel unit 41.

On the other hand, the embodiments are the same in that at least the coherent light source 11, the first speckle imaging unit 12, the second speckle imaging unit 13, and the image combination unit 14 are included, and furthermore, the embodiments are the same in that the analysis unit 15, the storage unit 16, the display unit 17, and the like may be included as necessary.

For this reason, in the following description of the imaging apparatus 401 according to the fourth embodiment, the description of the configuration common to the imaging apparatus 1 according to the first embodiment will be omitted. Hereinafter, the pixel unit 41 will be described.

(1) Pixel Unit

In the imaging apparatus 401 according to the fourth embodiment, each of the speckle imaging units 12 and 13 includes the pixel unit 41.

Each pixel unit 41 includes pixels each corresponding to each color component of a plurality of color components arrayed on a plane regularly.

In the imaging apparatus 401 of the present technology, the structure of the pixel unit 41 is not particularly limited. However, in order to increase the resolution of each captured speckle image, the Bayer matrix structure, which includes pixels corresponding to R, G, and B color components, may be preferably used.

Figure 5:
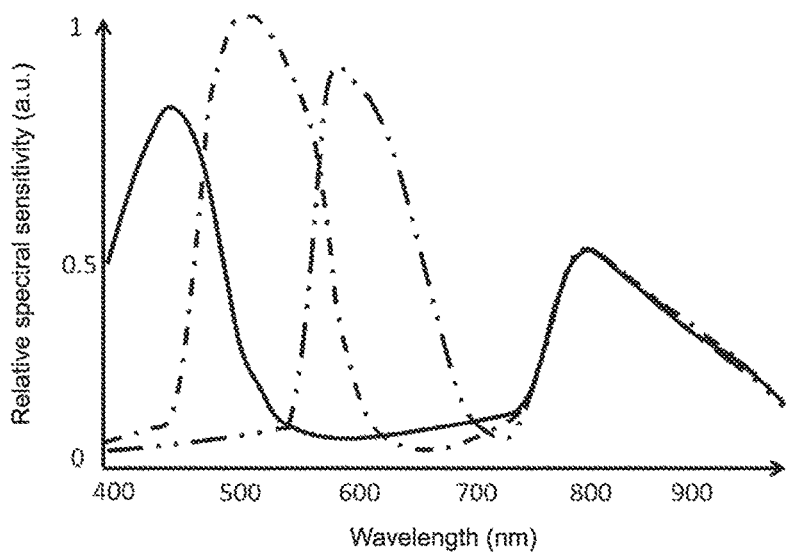
FIG. 5 is a diagram as a substitute for a graph, illustrating measurement results of relative spectral sensitivities of pixels of a pixel unit of the imaging apparatus of FIG. 4.

In this case, as shown in FIG. 5, with respect to each pixel corresponding to each of R, G, and B color components, the spectral sensitivity of each pixel with respect to the wavelength of speckle lighting is obtained. Then, the spectral sensitivity of each pixel may be corrected easily such that the spectral sensitivity of the pixels is uniform. Herein, in FIG. 5, the solid line shows the relative spectral sensitivity of the blue (B) color component, the dashed-chain line shows the relative spectral sensitivity of the green (G) color component, and the double-dashed-chain line shows the relative spectral sensitivity of the red color component. Note that, if the pixel unit 41 has the Bayer matrix, a method of interpolating pixels of the Bayer matrix is not particularly limited, and a known method may be used.

According to the imaging apparatus 401 of the fourth embodiment, each of the speckle imaging units 12 and 13 includes the pixel unit 41. According to the imaging apparatus 401 of the fourth embodiment, each pixel unit 41 has the Bayer matrix structure including pixels corresponding to R, G, and B color components. In this case, the spectral sensitivity of each of R, G, and B pixels may be corrected such that the spectral sensitivity is uniform. As a result, it is possible to obtain a speckle image by using R, G, and B pixel signals. Therefore, it is possible to increase the resolution of the first speckle image and the second speckle image.

5. Imaging System

The present technology also provides an imaging system.

Figure 6:
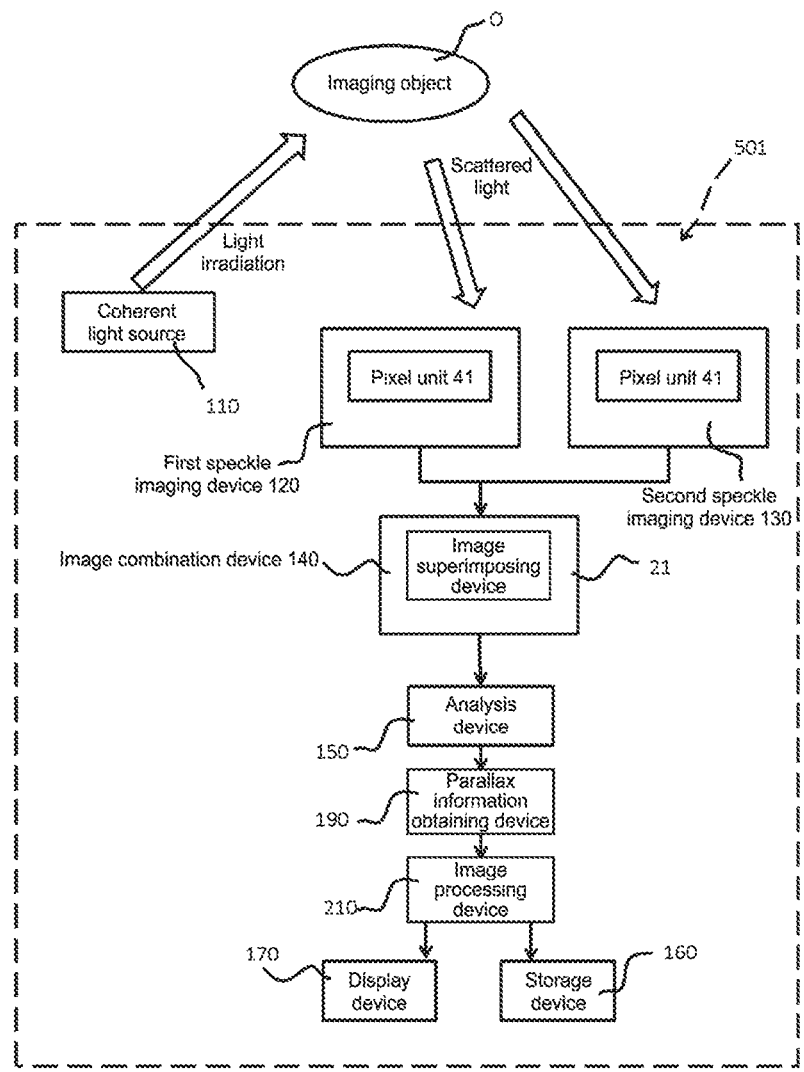
FIG. 6 is a schematic conceptual diagram schematically illustrating a concept of an imaging system according to the present technology.

FIG. 6 is a schematic conceptual diagram schematically illustrating an imaging system 501 according to the first embodiment of the present technology. The imaging system 501 includes at least a coherent light source 110, a first speckle imaging device 120, a second speckle imaging device 130, and an image combination device 140. In addition, as necessary, the imaging system 501 may further include an analysis device 150, a storage device 160, a display device 170, an image superimposing device 180, a parallax information obtaining device 190, and an image processing device 210. Each device will be described below.

(1) Coherent Light Source

The type of the coherent light source 110 is not particularly limited as long as the effect of the present technology is not impaired. As an example, laser light and the like may be exemplified. As the coherent light source 110 that emits laser light, an argon ion (Ar) laser, a helium-neon (He—Ne) laser, a dye laser, a krypton (Cr) laser, a semiconductor laser, a solid-state laser in which a semiconductor laser and a wavelength conversion optical element are combined, and the like may be exemplified, and one or two or more types thereof may be used freely in combination.

(2) First Speckle Imaging Device

The imaging system 501 according to the present technology includes a first speckle imaging device 120. In the speckle imaging device 130, speckle imaging is performed on the basis of scattered light obtained from the imaging object O irradiated with the coherent light. In the following description, a speckle image captured by the first speckle imaging device 120 will be referred to as "first speckle image".

The imaging method performed by the first speckle imaging device 120 is not particularly limited as long as the effect of the present technology is not impaired, and one or two or more known imaging methods may be selected and used freely in combination. For example, an imaging method using an imaging element such as a charge coupled device (CCD) or a complementary metal oxide semiconductor (CMOS) sensor may be exemplified.

Further, the first speckle imaging device 120 may include a pixel unit (not shown).

The pixel unit includes pixels each corresponding to each color component of a plurality of color components arrayed on a plane regularly. The structure of the pixel unit is not particularly limited. However, in order to increase the resolution of each captured speckle image, the Bayer matrix structure, which includes pixels corresponding to R, G, and B color components, may be preferably used.

In this case, with respect to each pixel corresponding to each of R, G, and B color components, the spectral sensitivity of each pixel with respect to the wavelength of speckle lighting is obtained. Then, the spectral sensitivity of each pixel may be corrected easily such that the spectral sensitivity is uniform.

In addition, the first speckle imaging device 120 may be configured to measure the luminance distribution of the speckle in the captured image. Herein, when an object illuminated by using coherent light is observed by the imaging optical system, speckle caused by scattering of the object on the image plane is observed. In the first speckle imaging device 120, the luminance distribution of the speckle in the captured image is measured by using, for example, a luminance meter. In addition, it is possible to calculate the speckle luminance distribution from an image captured from an imaging element such as a CCD or a CMOS.

The method of measuring the luminance distribution is not particularly limited as long as the effect of the present technology is not impaired, and one or two or more known calculation methods may be selected and used freely in combination.

In the first speckle imaging device 120, for example, an image or the like in which a pseudo blood vessel through which pseudo blood flows is mapped on the basis of the speckle luminance distribution is generated. Herein, since the speckle is a random interference/diffraction pattern as described above, when the scattering fluid such as blood moves or changes with time, the speckle also varies with time. For this reason, it is possible to observe the boundary between the fluid and other portions.

Note that, in order to further clarify the portion where speckle occurs, the first speckle imaging device 120 may have a configuration where, for example, equalization is performed by using a plurality of speckle images to reduce irregularity of the speckle image.

(3) Second Speckle Imaging Device

The imaging system 501 according to the present technology includes a second speckle imaging device 130. In the second speckle imaging device 130, similar to the first speckle imaging device 120, a speckle is captured on the basis of the scattered light obtained from the imaging object O which is irradiated with the coherent light. In other words, the imaging system 501 according to the present technology has a structure of a so-called pantoscopic imaging apparatus. In addition, each imaging unit is configured to capture a speckle image.

Further, the imaging system 501 according to the present technology has a so-called stereo camera system structure, in which the second speckle imaging device 130 and the first speckle imaging device 120 capture the imaging object O in different directions.

The structure of the second speckle imaging device 130 is the same as the structure of the first speckle imaging device 120, and description thereof will thus be omitted. Note that, in the following description, a speckle image captured by the second speckle imaging device 130 will be referred to as "second speckle image".

(4) Image Combination Device

The imaging system 501 according to the present technology includes an image combination device 140 as necessary. The image combination device 140 combines a first speckle image and a second speckle image. Specifically, for example, the image combination device 140 combines image information (for example, number of pixels, color tone of pixels, etc.) of the first speckle image and image information of the second speckle image to thereby generate a single speckle combined image.

Herein, it is necessary to generate a speckle combined image, with which it is possible to analyze the state of the imaging object O. When the image combination device 140 combines the first speckle image and the second speckle image, for example, the image combination device 140 may correct the luminance value of the speckle combined image on the basis of the luminance values of the speckle images such that the luminance distribution of the speckle combined image is uniform. The correcting method is not particularly limited, and a known method may be used.

(5) Analysis Device

The imaging system 501 according to the present technology may include an analysis device 150 as necessary. The analysis device 150 analyzes the state of the imaging object O by using the speckle combined image generated by the image combination device 140.

In such a case, for example, in a case where the imaging object O is a blood vessel, when the scattering fluid such as blood moves or changes with time, the speckle also varies with time accordingly. Therefore, the speed of the blood flow can be measured by the analysis device 150.

Note that the analysis device 150 is not necessarily included in the imaging system 501 according to the present technology, and the state of the imaging object O may also be analyzed by using an external analysis device or the like.

(6) Storage Device

The imaging system 501 according to the present technology may further include a storage device 160 that stores the speckle image captured by the first speckle imaging device 120, the non-speckle image captured by the second speckle imaging device 130, the speckle combined image generated by the image combination device 140, the analysis result analyzed by the analysis device 150, and the like.

The storage device 160 is not necessarily included in the imaging system 501 according to the present technology, but the imaging system may be connected to, for example, an external storage device to store the speckle image and the like.

(7) Display Unit Device

The imaging system 501 according to the present technology may further include a display device 170 that displays the speckle image captured by the first speckle imaging device 120, the non-speckle image captured by the second speckle imaging device 130, the speckle combined image generated by the image combination device 140, the analysis result analyzed by the analysis device 150, and the like. In addition, the display device 170 may display the luminance distribution measured by the first speckle imaging device 120 so as to be superimposed on the speckle image. The display device 170 is not necessarily included in the imaging system 501 according to the present technology, and light irradiation may be performed on the imaging object O by using, for example, an external monitor or the like.

(8) Image Superimposing Device

The imaging system 501 according to the present technology may include an image superimposing device 180 as necessary. When the image combination device 140 combines the first speckle image and the second speckle image, the image superimposing device 180 superimposes image information of the speckle images. The superimposing method is not particularly limited, and a known method may be used. For example, a method of adding and averaging speckle images may be used.

(9) Parallax Information Obtaining Device

As described above, the imaging system 501 of the present technology includes the first speckle imaging device 120 and the second speckle imaging device 130, i.e., two imaging devices, and employs a so-called stereo camera structure. So there is parallax between the two imaging devices.

The parallax information obtaining device 190 obtains information about the parallax. The parallax information means, for example, numerical data of parallax of each speckle image. The method of obtaining information of the parallax information obtaining device 190 is not particularly limited, and a known method may be used.

(10) Image Processing Device

In the imaging system 501 according to the present technology, if the imaging system 501 includes the parallax information obtaining device 190, the imaging system 501 preferably includes the image processing device 210.

The image processing device 210 is configured to obtain state information of the imaging object O on the basis of parallax information obtained by the parallax information obtaining device 190.

As described above, in the imaging system 501 according to the third embodiment, the display device 170 three-dimensionally displays the imaging object O in a stereo system. In this case, the display device 170 may three-dimensionally display the imaging object O only with horizontal parallax because vertical parallax is not captured.

In the imaging system 501 according to the present technology, the first speckle imaging device 120 and the second speckle imaging device 130, i.e., two imaging devices, are provided, and a so-called stereo camera structure is employed. So there is parallax between the two imaging devices. As a result, wavefront information of the imaging object O that reaches the first speckle imaging device 120 is different from wavefront information of the imaging object O that reaches the second speckle imaging device 130.

Therefore, the image noise resulting from the speckle shape of the first speckle image is different from the image noise resulting from the speckle shape of the second speckle image.

To the contrary, according to the present technology, the imaging system 501 includes the image combination device 140. The image combination device 140 combines the first speckle image and the second speckle image, and the noise is thus averaged. So the image noise of the speckle combined image may be reduced. As a result, it is possible to acquire the speckle combined image with high resolution.

Therefore, for example, when a blood vessel in which blood is flowing is imaged, a change of speckles according to temporal fluctuation of blood can be observed, so that it is possible to acquire an image by which it is possible to accurately recognize the flow path of the blood corpuscles. As a result, it is possible to accurately observe the relative position of the blood vessel to the biological tissue (for example, the heart or the like).

Further, according to the imaging system 501 of the present technology, both the imaging devices capture speckles. So, even if one imaging device does not work, the other imaging device may capture a speckle. As a result, a user may keep on observing the imaging object O. Further, even if the imaging system 501 according to the present technology includes the image superimposing device 180, it is possible to acquire the speckle combined image with high resolution.

Further, in the imaging system 501 according to the present technology, if the imaging system 501 includes the parallax information obtaining device 190 and the image processing device 210, the display device 170 may three-dimensionally display a speckle combined image only with horizontal parallax. Therefore, the imaging object O may be observed not only two-dimensionally but also three-dimensionally. Therefore, for example, when imaging blood that is scattering fluid, three-dimensional information of a blood vessel in which the blood flows may be obtained.

Further, according to the imaging system 501 of the present technology, if each of the speckle imaging devices 120 and 130 includes the pixel unit 41, each pixel unit 41 has the Bayer matrix structure including pixels corresponding to R, G, and B color components. In this case, the spectral sensitivity of each of R, G, and B pixels may be corrected such that the spectral sensitivity is uniform. As a result, it is possible to obtain a speckle image by using R, G, and B pixel signals. Therefore, it is possible to increase the resolution of the first speckle image and the second speckle image.

6. Imaging Method

The present technology also provides an imaging method.

Figure 7:
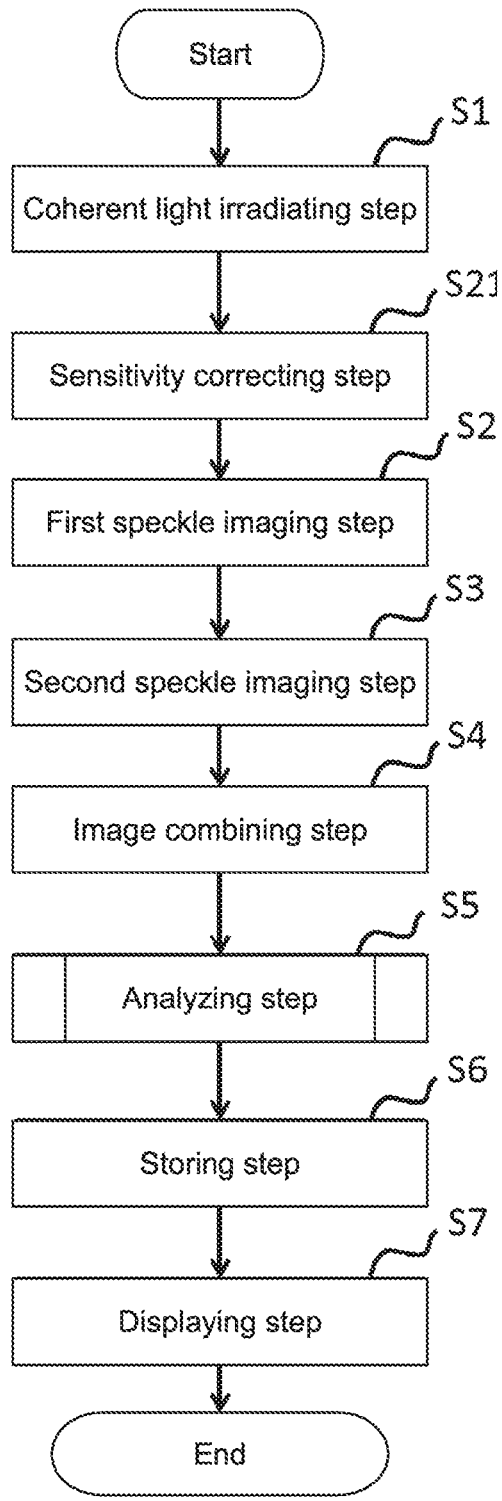
FIG. 7 is a flowchart of an imaging method according to the present technology.

FIG. 7 is a flowchart of an imaging method according to the present technology. The imaging method according to the first embodiment includes at least a coherent light irradiating step, a first speckle imaging step, a second speckle imaging step, and an image combining step. In addition, as necessary, the imaging method may further include an image superimposing step, a parallax information obtaining step, and an image processing step.

Note that, in FIG. 7, the analyzing step, the storing step, the displaying step, the image superimposing step, the parallax information obtaining step, and the image processing step are also illustrated, but as described above, these steps are not necessary steps. Therefore, these steps may not be performed in the imaging method according to the present technology. However, among the aforementioned steps, since a predetermined effect is exhibited by including the analyzing step, the storing step, the displaying step, the image superimposing step, the parallax information obtaining step, and the image processing step, it is desirable that these steps are included. The aforementioned steps will be described below in the order of executing the imaging method according to the present technology.

(1) Coherent Light Irradiating Step

In the imaging method according to the present technology, first, the imaging object O is irradiated with coherent light (coherent light irradiating step S1). Herein, the type of the coherent light source is not particularly limited as long as the effect of the present technology is not impaired. As an example, laser light and the like may be exemplified. As the coherent light source 11 that emits laser light, an argon ion (Ar) laser, a helium-neon (He—Ne) laser, a dye laser, a krypton (Cr) laser, a semiconductor laser, a solid-state laser in which a semiconductor laser and a wavelength conversion optical element are combined, and the like may be exemplified, and one or two or more types thereof may be used freely in combination.

(2) First Speckle Imaging Step

In the imaging method according to the present technology, after the coherent light irradiating step S1, on the basis of the scattered light obtained from the imaging object O irradiated with the coherent light, a first speckle image is captured.

The imaging method in the first speckle imaging step S2 is not particularly limited, and one or two or more known imaging methods may be selected and used freely in combination. For example, an imaging method using an imaging element such as a charge coupled device (CCD) or a complementary metal oxide semiconductor (CMOS) sensor may be exemplified.

(2-1) Sensitivity Correcting Step

In the imaging method of the present technology, the first speckle imaging step S2 may include a sensitivity correcting step S21 using the Bayer matrix including pixels corresponding to R, G, and B color components.

In other words, after completion of the coherent light irradiating step S1, when capturing a first speckle image is started, firstly, the spectral sensitivity of each pixel with respect to the wavelength of speckle lighting is obtained. Then, the spectral sensitivity of each pixel is corrected such that the spectral sensitivity of the pixels is uniform. Then, after completion of correction of the spectral sensitivity, a first speckle image is captured by using all the signals of the pixels.

(3) Second Speckle Imaging Step

In the imaging method of the present technology, after capturing a first speckle image, a second speckle image is captured. In other words, the imaging method of the present technology employs a so-called stereo system, in which the first speckle image and the second speckle image of the imaging object O are captured in different directions. The imaging method in the second speckle imaging step is the same as the imaging method in the first speckle imaging step, and description thereof will thus be omitted. Further, similar to the first speckle imaging step S2, the second speckle imaging step S3 may include the sensitivity correcting step using the Bayer matrix.

(4) Image Combination Step

The imaging method according to the present technology includes an image combining step S4 of combining the first speckle image captured in the first speckle imaging step S2 and the non-speckle image captured in the second speckle imaging step S3.

The image combining step S4 includes combining image information (for example, number of pixels, color tone of pixels, etc.) of the first speckle image and image information of the second speckle image to thereby generate a single speckle combined image.

Herein, it is necessary to generate a speckle combined image, with which it is possible to analyze the state of the imaging object O. When combining the first speckle image and the second speckle image, for example, the image combining step S4 may include correcting the luminance value of the speckle combined image on the basis of the luminance values of the speckle images such that the luminance distribution of the speckle combined image is uniform. The correcting method is not particularly limited, and a known method may be used.

In the imaging method of the present technology, the image combining step S4 may, without any problem, include superimposing the first speckle image and the second speckle image on each other to thereby generate a speckle superimposed image. The superimposing method is not particularly limited, and a known method may be used. For example, a method of adding and averaging speckle images may be used.

(5) Analyzing Step

Figure 8:
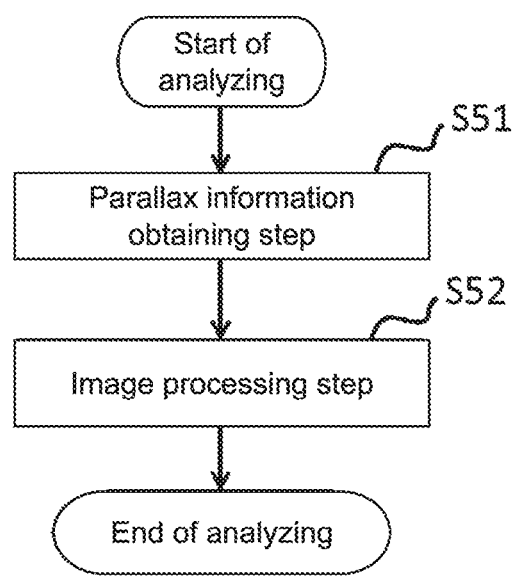
FIG. 8 shows a flowchart of an analyzing step of an imaging method according to the present technology in detail.

Next, with reference to FIG. 7 and FIG. 8, the analyzing step according to the imaging method of the present technology will be described. FIG. 8 is a flowchart showing the analyzing step S5 in detail.

In the analyzing step S5, the state of the imaging object O is analyzed by using the speckle combined image generated in the image combining step S4.

For example, in a case where the imaging object O is a blood vessel, when the scattering fluid such as blood moves or changes with time, the speckle also varies with time accordingly. Therefore, the speed of the blood flow can be measured in the analyzing step S5.

As shown in FIG. 8, the analyzing step S5 of the present technology may include a parallax information obtaining step S51 and an image processing step 52. Those steps will be described below.

(5-1) Parallax Information Obtaining Step

The imaging method of the present technology employs a stereo system, in which a first speckle image and a second speckle image of the imaging object O are captured in different directions. So there is parallax between the first speckle image and the second speckle image.

According to the imaging method of the present technology, when the analyzing step S5 is started, firstly, parallax information obtained in the first speckle imaging step S2 and the second speckle imaging step S3 is obtained. The parallax information means, for example, numerical data of parallax of each speckle image. The method of obtaining information in the parallax information obtaining step S51 is not particularly limited, and a known method may be used.

(5-2) Image Processing Step

According to the imaging method of the present technology, after the parallax information obtaining step S51, an image processing step S52 of obtaining state information of the imaging object O on the basis of the obtained parallax information is executed.

As described above, since the imaging method of the present technology employs the stereo system, in the image processing step S52, it is possible to analyze three-dimensional information of the imaging object O only with horizontal parallax out of the parallax information obtained in the parallax information obtaining step.

In the imaging method of the present technology, when the image processing step S52 is completed, the analyzing step S5 is completed.

(6) Storing Step

The imaging method according to the present technology may include, as necessary, a storing step S6.

The storing step S6 includes storing the speckle image captured in the first speckle imaging step S2, the non-speckle image captured in the second speckle imaging step S3, the speckle combined image generated in the image combining step S4, the analysis result analyzed in the analyzing step S5, and the like.

(7) Displaying Step

The imaging method according to the present technology may include a displaying step S7 as necessary.

In this displaying step S7, the speckle image captured in the first speckle imaging step S2, the non-speckle image captured in the second speckle imaging step S3, the speckle combined image generated in the image combining step S4, an analysis result analyzed in the analyzing step S5, and the like may be displayed.

Since the imaging method of the present technology includes the first speckle imaging step S2 and the second speckle imaging step S3 and employs a so-called stereo system, there is parallax between two speckle images.

As a result, the image noise resulting from the speckle shape of the first speckle image is different from the image noise resulting from the speckle shape of the second speckle image.

To the contrary, according to the present technology, the imaging method of the present technology includes the image combining step S4. The image combining step S4 includes combining the first speckle image and the second speckle image, and the noise is thus averaged. So the image noise of the speckle combined image may be reduced. As a result, it is possible to acquire the speckle combined image with high resolution.

Therefore, for example, when a blood vessel in which blood is flowing is imaged, a change of speckles according to temporal fluctuation of blood can be observed, so that it is possible to acquire an image by which it is possible to accurately recognize the flow path of the blood corpuscles. As a result, it is possible to accurately observe the relative position of the blood vessel to the biological tissue (for example, the heart or the like).

Further, if the imaging method of the present technology includes the parallax information obtaining step S51 and the image processing step S52, it is possible to three-dimensionally display a speckle combined image only with horizontal parallax. Therefore, the imaging object O may be observed not only two-dimensionally but also three-dimensionally. Therefore, for example, when imaging blood that is scattering fluid, three-dimensional information of a blood vessel in which the blood flows may be obtained.

Further, in the imaging method of the present technology, each speckle imaging step may include the sensitivity correcting step S21 using the Bayer matrix. In this case, the spectral sensitivities of R, G, and B pixels are corrected such that the spectral sensitivity is uniform. As a result, it is possible to obtain a speckle image by using all the pixel signals. As a result, it is possible to increase the resolution of the first speckle image and the second speckle image.

In addition, the imaging apparatus according to the present technology may also have the following configurations.
(1) An imaging apparatus, including:
a coherent light source that irradiates an imaging object with coherent light;
a first speckle imaging unit that captures a speckle image obtained from scattered light of the imaging object irradiated with the coherent light;
a second speckle imaging unit that captures a speckle image obtained from scattered light of the imaging object irradiated with the coherent light; and
an image combination unit that combines the first speckle image captured by the first speckle imaging unit and the second speckle image captured by the second speckle imaging unit.
(2) The imaging apparatus according to (1), further including:
an image superimposing unit that superimposes image information of the first speckle image and image information of the second speckle image on each other.
(3) The imaging apparatus according to (1) or (2), further including:
a parallax information obtaining unit that obtains parallax information generated between the first speckle imaging unit and the second speckle imaging unit; and
an image processing unit that obtains state information of the imaging object on the basis of the parallax information obtained by the parallax information obtaining unit.
(4) The imaging apparatus according to any one of (1) to (3), in which
each of the first speckle imaging unit and second speckle imaging unit includes a pixel unit, the pixel unit including pixels each corresponding to each color component of a plurality of color components arrayed on a plane regularly.
(5) The imaging apparatus according to (4), in which
the pixel unit is a pixel unit of Bayer matrix.

In addition, the imaging system according to the present technology may also have the following configurations.
(6) An imaging system, including:
a coherent light source that irradiates an imaging object with coherent light;
a first speckle imaging device that captures a speckle image obtained from scattered light of the imaging object irradiated with the coherent light;
a second speckle imaging device that captures a speckle image obtained from scattered light of the imaging object irradiated with the coherent light; and
an image combination device that combines the first speckle image captured by the first speckle imaging device and the second speckle image captured by the second speckle imaging device.
(7) The imaging system according to (6),
an image superimposing device that superimposes image information of the first speckle image and image information of the second speckle image on each other.
(8) The imaging system according to (6) or (7), further including:
a parallax information obtaining device that obtains parallax information generated between the first speckle imaging device and the second speckle imaging device; and
an image processing device that obtains state information of the imaging object on the basis of the parallax information obtained by the parallax information obtaining device.
(9) The imaging system according to any one of (6) to (8), in which
each of the first speckle imaging device and second speckle imaging device includes a pixel unit, the pixel unit including pixels each corresponding to each color component of a plurality of color components arrayed on a plane regularly.
(10) The imaging system according to (9), in which
the pixel unit is a pixel unit of Bayer matrix.

REFERENCE SIGNS LIST

1, 101, 201, 301, 401 imaging apparatus
11 coherent light source
12 first speckle imaging unit
13 second speckle imaging unit
14 image combination unit

The invention claimed is:
1. An imaging apparatus, comprising:
a coherent light source configured to irradiate an imaging object with coherent light;
a first imaging sensor configured to capture a first speckle image obtained from scattered light of the imaging object irradiated with the coherent light;
a second imaging sensor configured to capture a second speckle image obtained from the scattered light of the imaging object irradiated with the coherent light; and
circuitry configured to:
combine the first speckle image and the second speckle image to generate a speckle combined image;

correct, based on luminance values of the first speckle image and the second speckle image, a luminance value of the speckle combined image such that a luminance distribution of the speckle combined image is uniform;

measure a luminance distribution of a speckle in the first speckle image; and display, on a display screen, the measured luminance distribution superimposed on the first speckle image.

2. The imaging apparatus according to claim 1, wherein the circuitry is further configured to superimpose image information of the first speckle image and image information of the second speckle image on each other.

3. The imaging apparatus according to claim 1, wherein the circuitry is further configured to:

obtain parallax information between the first imaging sensor and the second imaging sensor; and obtain state information of the imaging object based on the parallax information.

4. The imaging apparatus according to claim 1, wherein each of the first imaging sensor and the second imaging sensor includes a pixel unit, the pixel unit includes a plurality of pixels, and each pixel of the plurality of pixels corresponds to each color component of a plurality of color components arrayed on a plane regularly.

5. The imaging apparatus according to claim 4, wherein the pixel unit has a Bayer matrix structure.

6. An imaging system, comprising:

a coherent light source configured to irradiate an imaging object with coherent light;

a first speckle imaging device configured to:

capture a first speckle image obtained from scattered light of the imaging object irradiated with the coherent light; and measure a luminance distribution of a speckle in the first speckle image;

a display screen configured to display the measured luminance distribution superimposed on the first speckle image;

a second speckle imaging device configured to capture a second speckle image obtained from the scattered light of the imaging object irradiated with the coherent light; and an image combination device configured to:

combine the first speckle image and the second speckle image to generate a speckle combined image; and correct, based on luminance values of the first speckle image and the second speckle image, a luminance value of the speckle combined image such that a luminance distribution of the speckle combined image is uniform.

7. The imaging system according to claim 6, further comprising an image superimposing device configured to superimpose image information of the first speckle image and image information of the second speckle image on each other.

8. The imaging system according to claim 6, further comprising:

a parallax information obtaining device configured to obtain parallax information between the first speckle imaging device and the second speckle imaging device; and an image processing device configured to obtain state information of the imaging object based on the parallax information.

9. The imaging system according to claim 6, wherein each of the first speckle imaging device and the second speckle imaging device includes a pixel unit, the pixel unit includes a plurality of pixels, and each pixel of the plurality of pixels corresponds to each color component of a plurality of color components arrayed on a plane regularly.

10. The imaging system according to claim 9, wherein the pixel unit has a Bayer matrix structure.

11. An imaging method, comprising:

in an imaging apparatus that comprises a coherent light source, a first imaging sensor, a second imaging sensor, and circuitry:

irradiating, by the coherent light source, an imaging object with coherent light;

capturing, by the first imaging sensor, a first speckle image obtained from scattered light of the imaging object irradiated with the coherent light;

measuring, by the circuitry, a luminance distribution of a speckle in the first speckle image;

displaying, on a display screen, by the circuitry, the measured luminance distribution superimposed on the first speckle image;

capturing, by the second imaging sensor, a second speckle image obtained from the scattered light of the imaging object irradiated with the coherent light;

combining, by the circuitry, the first speckle image and the second speckle image to generate a speckle combined image; and correcting, by the circuitry based on luminance values of the first speckle image and the second speckle image, a luminance value of the speckle combined image such that a luminance distribution of the speckle combined image is uniform.

* * * * *